United States Patent

Cohnen et al.

Patent Number: 4,594,419
Date of Patent: Jun. 10, 1986

[54] SUBSTITUTED 5-PHENYLTHIO-6-AMINO-PYRIMIDINONES, A PROCESS FOR THEIR PREPARATION AND THEIR USE, AND FORMULATIONS CONTAINING THESE COMPOUNDS

[75] Inventors: Erich Cohnen, Jork; Ben Armah, Hamburg, both of Fed. Rep. of Germany

[73] Assignee: Beiersdorf Aktiengesellschaft, Hamburg, Fed. Rep. of Germany

[21] Appl. No.: 503,469

[22] Filed: Jun. 13, 1983

[30] Foreign Application Priority Data

Jun. 18, 1982 [DE] Fed. Rep. of Germany ....... 3222914

[51] Int. Cl.$^4$ .................................... C07D 239/10
[52] U.S. Cl. ................................ 544/311; 544/321
[58] Field of Search ............... 544/311, 321; 514/269, 514/272

[56] References Cited

U.S. PATENT DOCUMENTS 3,337,543  8/1967  Roth et al. ......................... 544/298

FOREIGN PATENT DOCUMENTS 2329399  1/1975  Fed. Rep. of Germany.
990857  5/1965  United Kingdom.

*Primary Examiner*—Donald G. Daus
*Assistant Examiner*—Stephen M. Kapner
*Attorney, Agent, or Firm*—Sprung Horn Kramer & Woods

[57] ABSTRACT

Substituted 5-phenylthio-6-aminopyrimidinones of the general formula I

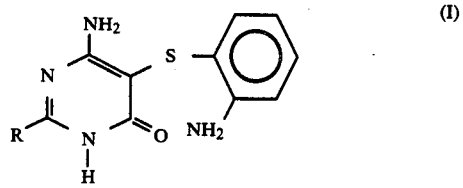

in which R denotes an amino or hydroxyl group, and their tautomeric forms and acid addition salts thereof, have diuretic, saluretic and uricosuric actions. They can be used as medicaments for the treatment of hypertension, hyperuricemia and edemas.

2 Claims, No Drawings

SUBSTITUTED 5-PHENYLTHIO-6-AMINO-PYRIMIDINONES, A PROCESS FOR THEIR PREPARATION AND THEIR USE, AND FORMULATIONS CONTAINING THESE COMPOUNDS

The invention relates to substituted 5-phenylthio-6-amino-pyrimidinones of the general formula I

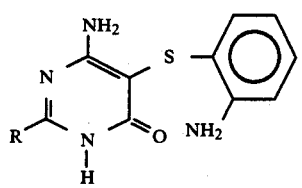

in which R denotes an amino or hydroxyl group, as well as their tautomeric forms and acid addition salts thereof, a process for their preparation and their use in pharmaceutical products.

For simplicity, the compounds according to the invention are defined in only one tautomeric form, represented by formula I. However, the invention relates to all tautomeric forms of the compounds, especially to the pyrimidinedione.

Although pharmaceutically acceptable salts of the novel compounds of the formula I and tautomeric forms thereof are preferred, all the acid addition salts lie within the scope of the invention. All the acid addition salts are useful for the preparation of the bases, even if the particular salt is required only as an intermediate, such as, for example, if the salt is formed only for the purpose of purification or identification, or if it is used as an intermediate in the preparation of a pharmaceutically acceptable salt, for example by ion exchange procedures.

The following compounds of the general formula I and salts thereof are particularly preferred:

6-Amino-5-(2-amino-phenylthio)-2,4(1H,3H)-pyrimidinedione. This compound and its tautomeric forms are novel.

2,6-Diamino-5-(2-amino-phenylthio)-4(1H)-pyrimidinone. This compound and its tautomeric forms are novel, with the exception of 2,4-diamino-5-(2-amino-phenylthio)-6-hydroxypyrimidine.

The compound 2,4-diamino-5-(2-aminophenylthio)-6-hydroxypyrimidine is known as an intermediate from British Patent Specification No. 990,857. No intended therapeutic use is stated.

The compounds according to the invention have pronounced diuretic, saluretic and uricosuric actions and can therefore be used for the treatment of hypertension, hyperuricemia and edemas.

The compounds of the present invention can be used orally or parenterally on humans, preferably in a dosage of 250–1,000 mg per day, in particular in divided doses, for example twice daily.

Daily doses of 500–1,000 mg, divided into two administrations, are preferred for the treatment of hypertension. This dosage also applies to the treatment of edemas. Hyperuricemia is preferably treated with 250 mg to 500 mg per day.

Pharmaceutical formulations containing a compound of the formula I, in which R denotes an amino or hydroxyl group, or pharmaceutically acceptable salts thereof, together with a pharmaceutically acceptable diluent or excipient, are provided according to the invention.

The compounds according to the invention can be mixed with the conventional pharmaceutically acceptable diluents or excipients, and if appropriate with other auxiliaries, and can be administered, for example, orally or parenterally. They can be administered orally in the form of tablets, dragees, syrups, suspensions and liquids, or parenterally in the form of solutions or suspensions. Products to be administered orally can contain one or more additives, such as sweeteners, aromatizing agents, colorants and preservatives. Tablets can contain the active ingredient mixed with conventional pharmaceutically acceptable auxiliaries, for example inert diluents, such as calcium carbonate, sodium carbonate, lactose and talc, granulating agents and agents which promote disintegration of the tablets on oral administration, such as starch or alginic acid, binders, such as starch or gelatine, and lubricants, such as magnesium stearate, stearic acid and talc.

Examples of suitable excipients are milk sugar (lactose), gelatin, corn starch, stearic acid, ethanol, propylene glycol, ethers of tetrahydrofuryl alcohol and water.

The tablets can be coated by known procedures in order to delay disintegration and absorption in the gastrointestinal tract, by which means the activity of the active ingredient can be extended over a longer period of time. In suspensions, the active ingredient can likewise be mixed with the conventional auxiliaries for the preparation of such compositions, for example suspending agents, such as methylcellulose, tragacanth or sodium alginate, wetting agents, such as lecithin, polyethylene stearate and polyoxyethylene sorbitan monooleate, and preservatives, such as ethyl p-hydroxybenzoate. Capsules can contain the active ingredient as the sole constituent or mixed with a solid diluent, such as calcium carbonate, calcium phosphate or kaolin. Injectable products are likewise formulated in a manner which is known per se. The pharmaceutical products can contain the active ingredient in an amount of 0.1 to 90%, in particular 1 to 90%, the remainder being an excipient or additive. Solid products, such as tablets and capsules, are preferred from the point of view of preparation and administration. The products preferably contain 250 mg of the active ingredient.

The pyrimidinones of the general formula I according to the invention, in which R denotes an amino or hydroxyl group, are prepared by reacting 5-bromo-pyrimidinones of the general formula II

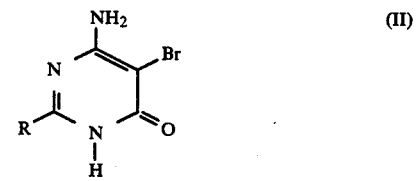

in which R has the abovementioned meaning, with 2-aminothiophenol in the presence of bases, for example potassium carbonate, in an inert organic solvent at temperatures between 150° and 200° C.

The bromopyrimidinones of the general formula II used as starting compounds are compounds described in the literature.

The compounds of the general formula I can be isolated from the reaction mixtures either as bases or in the form of their salts.

As bases, they can be converted into salts by known processes with suitable inorganic or organic acids. Physiologically acceptable salts are preferred. For these salts, examples of suitable inorganic acids are the hydrogen halide acids, for example hydrochloric acid, or sulfuric acid, and examples of suitable organic acids are fumaric acid and maleic acid. For the preparation, an alcoholic solution of a suitable acid is added to a hot alkaline solution of the base and, after addition of either, the salt is obtained.

The examples which follow serve to illustrate the invention:

EXAMPLE 1

6-Amino-5-(2-amino-phenylthio)-2,4(1H,3H)-pyrimidinedione (R=OH)

10.3 g of 6-amino-5-bromo-2,4(1H,3H)-pyrimidinedione, 7.0 g of potassium carbonate and 9.0 g of 2-aminothiophenol in 150 ml of ethylene glycol are heated at 170° C. under a nitrogen atmosphere for 4 hours. After filtration, the reaction mixture is poured onto 400 ml of water and decanted from the oily residue. After acidification with acetic acid, 4 g of 6-amino-5-(2-amino-phenylthio)-2,4(1H,3H)-pyrimidinedione are obtained, and are purified by recrystallization from ethanol/water.

Melting point >310° C.

IR spectrum (KBr): 3450, 3360, 3200 cm$^{-1}$ (NH$_2$, NH) 1710 and 1620 cm$^{-1}$ (C=O, C=N—).

The hydrochloride is prepared in the following manner: the base is dissolved in methanol, ethanolic hydrochloric acid is added until an acid reaction is obtained and the 6-amino-5-(2-amino-phenylthio)-2,4(1H,3H)-pyrimidinedione hydrochloride, which is sparingly soluble in methanol, is filtered off.

Melting point >300° C.

EXAMPLE 2

2,6-Diamino-5-(2-amino-phenylthio)-4(1H)-pyrimidinone (R=NH$_2$)

2,6-Diamino-5-(2-amino-phenylthio)-4(1H)-pyrimidinone is prepared analogously to Example 1, starting from 2,6-diamino-5-bromo-4(1H)-pyrimidinone.

Melting point 294°–295° C. (decomposition).

IR spectrum (KBr): 3430, 3370, 3150 cm$^{-1}$ (NH$_2$, NH) and 1620 cm$^{-1}$ (C=O), (C=N—).

EXAMPLE 3

Preparation of tablets

Tablets containing the constituents shown below are prepared by known procedures. These are suitable for the treatment of hypertension and edemas when administered in a dosage of 250 mg twice daily, and for the treatment of hyperuricemia when administered in an amount of 250 mg once daily.

6-Amino-5-(2-amino-phenylthio)-2,4(1H,3H)-pyrimidinedione: 250 mg Lactose: 448 mg Corn starch: 50 mg Magnesium stearate: 2 mg

We claim:

1. A substituted 5-phenylthio-6-amino-pyrimidinone of the formula

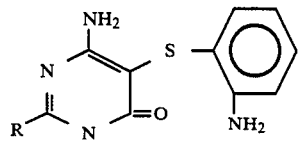

in which R denotes a hydroxyl group, and its tautomers and acid addition salts.

2. A compound of claim 1 which is 6-Amino-5-(2-amino-phenylthio)-2,4-(1H,3H)-pyrimidinedione.